(12) United States Patent
Qiu

(10) Patent No.: US 9,057,692 B2
(45) Date of Patent: Jun. 16, 2015

(54) DEVICE FOR MEASURING REFRACTIVE INDEX OF MEDIUM BASED ON OPTICAL DELAY TECHNOLOGY AND ITS METHOD

(71) Applicant: University of Electronic Science and Technology of China, Chengdu, Sichuan (CN)

(72) Inventor: Qi Qiu, Sichuan (CN)

(73) Assignee: University of Electronic Science and Technology of China, Chengdu, Sichuan Province (CN)

( * ) Notice: Subject to any disclaimer, the term of this patent is extended or adjusted under 35 U.S.C. 154(b) by 0 days.

(21) Appl. No.: 14/067,871

(22) Filed: Oct. 30, 2013

(65) Prior Publication Data

US 2014/0118726 A1    May 1, 2014

(30) Foreign Application Priority Data

Oct. 31, 2012   (CN) .......................... 2012 1 0425600

(51) Int. Cl.
*G01N 21/41*   (2006.01)
(52) U.S. Cl.
CPC ...................................... *G01N 21/41* (2013.01)
(58) Field of Classification Search
CPC ..... G01N 21/255; G01N 21/41; G01N 21/59; G01N 2201/0696
USPC ........ 356/128–137; 351/211, 212, 214, 96.11
See application file for complete search history.

(56) References Cited

U.S. PATENT DOCUMENTS

| | | | |
|---|---|---|---|
| 4,632,528 A | | 12/1986 | Yoshino et al. |
| 4,679,936 A | * | 7/1987 | Gerharz ........................ 356/128 |
| 4,950,074 A | * | 8/1990 | Fabricius et al. ............. 356/133 |
| 2004/0130706 A1 | | 7/2004 | Frot |

* cited by examiner

*Primary Examiner* — Tri T Ton

(57) ABSTRACT

A device for measuring refractive index of medium based on optical delay technology comprises: a signal processing and controlling module, an optical transmitter module, and an optical receiver module, wherein the signal processing and controlling module controls the optical transmitter module to transmit an optical signal having a certain wavelength; the optical signal is injected into a medium to be measured; the optical signal is transmitted and delayed by the medium; the optical receiver module receives the optical signal delayed, and transforms the optical signal delayed into a electrical signal; the electrical signal is amplified and transmitted to the signal processing and controlling module; the signal processing and controlling module measures a delay time between transmitting and receiving the optical signal; and the refractive index of the medium at the certain wavelength is calculated based on the delay time and a known length of the medium.

2 Claims, 1 Drawing Sheet

DEVICE FOR MEASURING REFRACTIVE INDEX OF MEDIUM BASED ON OPTICAL DELAY TECHNOLOGY AND ITS METHOD

BACKGROUND OF THE PRESENT INVENTION

1. Field of Invention

The present invention relates to a field of optoelectronic technology, and more particularly to a device for measuring refractive index of medium based on optical delay technology and its method.

2. Description of Related Arts

Methods for measuring refractive index of medium can be divided in two types, i.e., the transmission type and the reflection type.

In the transmission-type method, the refractive index of medium to be measured is calculated based on the characteristic of the transmitted light which has passed through the medium to be measured. The transmission-type method mainly comprises: measuring the angle of incidence of the incident ray and the angle of refraction of the refracted ray; and calculating the refractive index according to the formula of law of refraction, also called Snell's law. The transmission-type method is simple and easy to realize. The measuring accuracy depends on accurate measurement of the angle of incidence and the angle of refraction, and the measuring device is complicated. Meanwhile, the medium to be measured is required to be the optically transparent medium, such as water, glass, and crystal. The transmission-type method is not applicable for the turbid medium, such as milk which is a liquid, because the light passing through the medium will be scattered and absorbed.

In the reflection-type method, the refractive index of medium to be measured is calculated based on the parameters of light reflection characteristic, such as reflectivity, polarization, phase and critical angle, wherein the reflection happens at the medium interface. The critical angle method is typical in the reflection-type method. According to the law of refraction, when the light passes through the optically thinner medium from the optically denser medium, the angle of refraction is larger than the angle of incidence. In addition, when the angle of incidence increases, the angle of refraction will increase. When the angle of incidence increases to a certain value, the angle of refraction will increase to 90 degrees, which means that the refracted ray propagates along the interface between the two media. The angle of incidence in this case is called critical angle. If the angle of incidence continues to increase after achieving the critical angle, the light will not propagate into the optically thinner medium. Instead, the light is completely reflected back to the optically denser medium, which is a phenomenon known as total reflection. When the refractive index of the optically denser medium does not change, the critical angle only depends on the refractive index of the optically thinner medium. The device designed based on this method is called critical angle refractometer. The measuring method has a simple principle. The measuring accuracy depends on accurate measurement of the angle. The device is complicated, but the device is widely applicable for many measuring objects, comprising non-transparent medium, translucid medium, and transparent medium, for example, metal, milk, etc.

SUMMARY OF THE PRESENT INVENTION

In order to solve above problems in conventional technology, the present invention provides a device for measuring refractive index of medium based on optical delay technology and its method. An object of the present invention is to solve a technical problem in conventional methods for measuring refractive index of medium that angles of light are required to be measured accurately. However, a measuring system for measuring the angles of light is complicated, high in cost, and low in efficiency.

A principle of the present invention is as follows. In control of signal processing and controlling module, a first electrical signal is modulated onto an optical carrier by an optical transmitter module. The optical transmitter module transmits an optical signal having a certain wavelength, and the optical signal is injected into a medium to be measured and propagates therein. The optical signal which is delayed arrives at an optical receiver module, and then is transformed into a second electrical signal. The electrical signal is amplified and transmitted to the signal processing and controlling module. The signal processing and controlling module measures a delay time between transmitting the optical signal and receiving the optical signal. Accordingly, refractive index of the medium to be measured at the certain wavelength is calculated based on a known length of the medium to be measured and the delay time. For example, if an optical signal having a certain wavelength $\lambda_0$ propagates in a medium, the optical signal will be delayed by the medium. A delay time is calculated by $\Delta t=(L \cdot n)/c$, wherein $\Delta t$ refers to the delay time, L refers to a length of transmission path in the medium, and n refers to refractive index of the medium at the wavelength $\lambda_0$, and c refers to velocity of light in vacuum, which is a constant 300000 km/s. Thus it can be seen that the refractive index n of the medium at the wavelength $\lambda_0$ can be calculated based on the delay time measured accurately and the known length of the medium L, and $n=(c \cdot \Delta t)/L$.

In order to solve the above technical problems, a technical solution of the present invention is as follows.

A device for measuring refractive index of medium based on optical delay technology comprises: a signal processing and controlling module, an optical transmitter module, and an optical receiver module, wherein the signal processing and controlling module controls the optical transmitter module to transmit an optical signal having a certain wavelength; the optical signal is injected into a medium to be measured; the optical signal is transmitted in the medium to be measured and delayed by the medium to be measured; after the optical signal delayed arrives at the optical receiver module, the optical receiver module transforms the optical signal delayed into a second electrical signal, and the second electrical signal is amplified and transmitted to the signal processing and controlling module by the optical receiver module; the signal processing and controlling module measures a delay time between transmitting the optical signal and receiving the optical signal; the refractive index of the medium to be measured at the certain wavelength is calculated based on the delay time and a known length of the medium to be measured.

The optical transmitter module is preferably a semiconductor laser or a solid laser, able to transmit an optical signal having a certain wavelength. After direct intensity modulation or indirect intensity modulation, the optical transmitter module transmits an optical signal in a shape of continuous sine or pulse, and injects the optical signal into the medium to be measured.

The optical receiver module is preferably a PIN photoelectric detector or an APD photoelectric detector, which detects the optical signal transmitted and delayed by the medium to be measured. The optical receiver module receives the optical signal delayed having a wavelength matching with the wavelength of the optical signal transmitted by the optical transmitter module, and transforms the optical signal delayed into the second electrical signal. The second electrical signal is amplified, output, and transmitted to the signal processing and controlling module by the optical receiver module.

The medium to be measured is a medium through which the optical signal is able to pass, for example, glass, crystalline material, silica fiber, plastic fiber, etc.

The signal processing and controlling module comprises an analog circuit and a digital circuit, both of which have high accuracy, to generate a first electrical signal and control to transmit the first electrical signal. The signal processing and controlling module measures the delay time between transmitting the optical signal and receiving the optical signal, according to which the refractive index is calculated.

The present invention provides a measuring method with a device for measuring refractive index of medium based on optical delay technology, which comprises:

(1) measuring a first delay time of an etalon, i.e., $t_1$, with the device for measuring refractive index of medium based on optical delay technology, wherein a refractive index and a length of the etalon are respectively known as $n_1$ and $L_1$;

(2) replacing the etalon with a medium to be measured, and measuring a second delay time $t_2$ with other factors unchanged, wherein a refractive index and a length of the medium to be measured are respectively denoted as $n_2$ and $L_2$;

(3) calculating an additional delay time of an optical signal with $\Delta t = t_1 - t_2$, wherein the additional delay time is caused by the medium to be measured; and (4) calculating the refractive index $n_2$ of the medium to be measured with a formula, i.e., $\Delta t = (n_1 \cdot L_1 - n_2 \cdot L_2)/c$, wherein $n_2 = (n_1 \cdot L_1 - c \cdot \Delta t)/L_2$.

The etalon is a medium having the refractive index and the known length, wherein the etalon is preferably air or vacuum.

Compared to conventional technology, beneficial effects of the present invention are as follows.

Firstly, optical system is simple and easy to operate. The optical system transforms measuring of optical parameters into measuring of optoelectronic signals, in order to decrease complexity of measuring system.

Secondly, the device in the present invention is low in cost, and easy to popularize and apply.

Thirdly, the measuring method and measuring steps in the present invention eliminate affection of circuit system, and increase accuracy of measuring.

These and other objectives, features, and advantages of the present invention will become apparent from the following detailed description, the accompanying drawings, and the appended claims.

DETAILED DESCRIPTION OF THE PREFERRED EMBODIMENT

Figure 1:
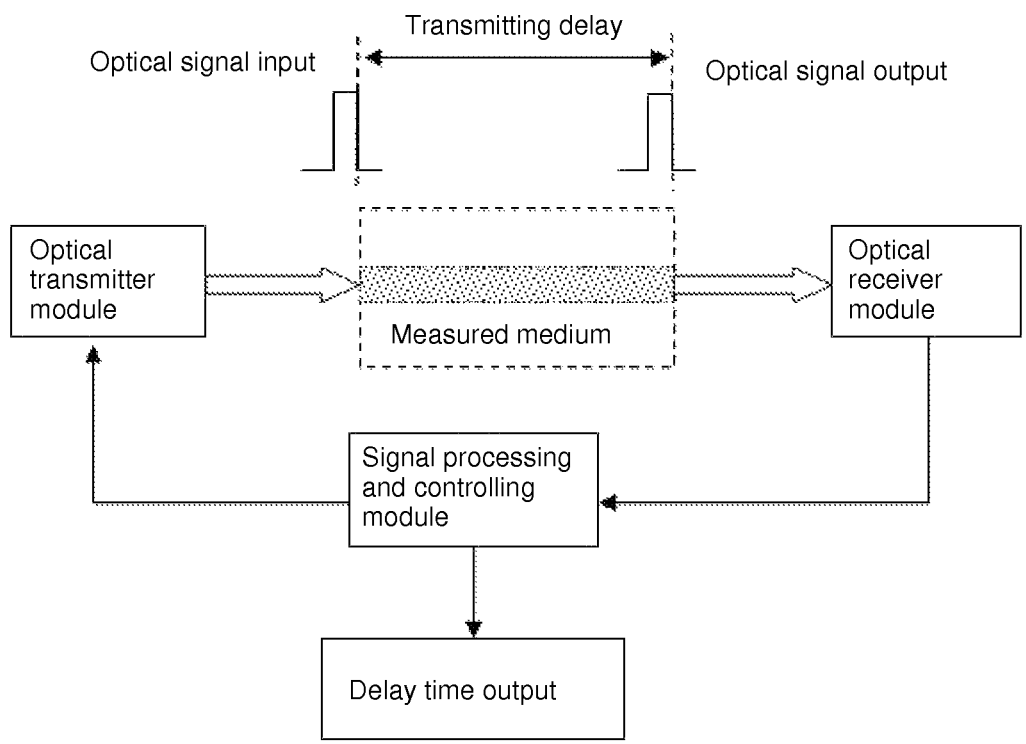
FIG. 1 is a sketch view of structure of a device for measuring refractive index of medium based on optical delay technology according to a preferred embodiment of the present invention.

Referring to the drawings, the preferred embodiment of the present invention is further described as follows.

Referring to FIG. 1, a device for measuring refractive index of medium based on optical delay technology comprises a signal processing and controlling module, an optical transmitter module, and an optical receiver module, wherein the signal processing and controlling module controls the optical transmitter module to transmit an optical signal having a certain wavelength; the optical signal is injected into the medium to be measured; the optical signal is transmitted in the medium to be measured and delayed by the medium to be measured; after the optical signal delayed arrives at the optical receiver module, the optical receiver module transforms the optical signal delayed into a second electrical signal, and the second electrical signal is amplified and transmitted to the signal processing and controlling module by the optical receiver module; the signal processing and controlling module measures a delay time between transmitting the optical signal and receiving the optical signal; the refractive index of the medium to be measured at the certain wavelength is calculated according to the delay time and a known length of the medium to be measured.

Embodiment

The optical transmitter module is embodied as a 1.55 µm semiconductor laser. After direct intensity modulation, the optical transmitter module transmits an optical pulse signal. The medium to be measured is embodied as silica fiber. The optical receiver module comprises a PIN photoelectric detector having a waveband of 1.55 µm, a pre-amplifier, and a main amplifier; wherein the optical receiver module detects the optical signal transmitted and delayed by the silica fiber to be measured, and transforms the optical signal into the second electrical signal; and the electrical signal is amplified, output, and transmitted to the signal processing and controlling module by the optical receiver module. The signal processing and controlling module comprises an analog circuit and a digital circuit, both of which have high accuracy, to generate a first electrical signal and control to transmit a first electrical signal; wherein the signal processing and controlling module measures the delay time between transmitting the optical signal and receiving the optical signal; and the refractive index of the silica fiber at the wavelength of 1.55 µm is calculated according to the delay time and the known length of the silica fiber to be measured.

Figure 2:
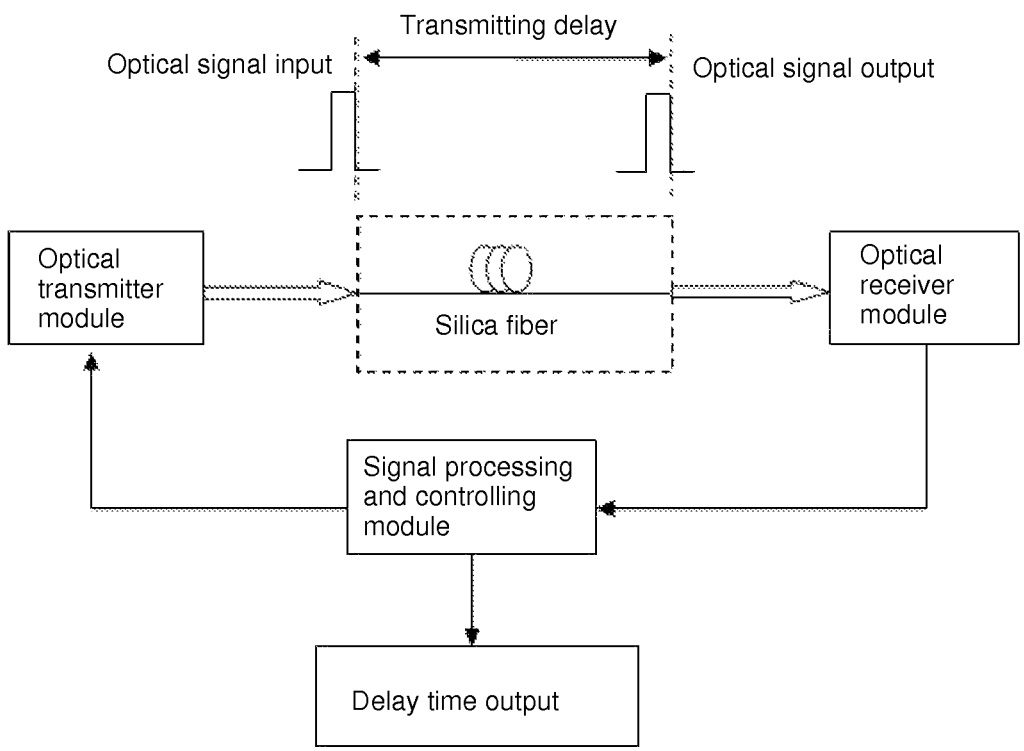
FIG. 2 is a sketch view of the device for measuring refractive index of medium according to the preferred embodiment of the present invention, wherein the medium is silica fiber.

The delay time of the optical signal is accurately measured by steps of:

(1) measuring a first delay time of silica fiber, i.e., $t_1$, with the device for measuring refractive index of medium based on optical delay technology as shown in FIG. 2, wherein a refractive index and a length of the silica fiber are respectively known as $n_1$ and $L_1$;

(2) replacing the silica fiber with a fiber to be measured, and measuring a second delay time $t_2$ with other factors unchanged, wherein a refractive index and a length of the fiber to be measured are respectively denoted as $n_2$ and $L_2$;

(3) calculating an additional delay time of the optical signal with $\Delta t = t_1 - t_2$, wherein the additional delay time is caused by the fiber to be measured; and (4) calculating the refractive index $n_2$ of the fiber to be measured with a formula, i.e., $\Delta t = (n_1 \cdot L_1 - n_2 \cdot L_2)/c$, wherein $n_2 = (n_1 \cdot L_1 - c \cdot \Delta t)/L_2$.

One skilled in the art will understand that the embodiment of the present invention as shown in the drawings and described above is exemplary only and not intended to be limiting.

It will thus be seen that the objects of the present invention have been fully and effectively accomplished. Its embodiments have been shown and described for the purposes of illustrating the functional and structural principles of the present invention and is subject to change without departure from such principles. Therefore, this invention includes all modifications encompassed within the spirit and scope of the following claims.

What is claimed is:

1. A measuring method with the device for measuring refractive index of medium based on optical delay technology comprising: a signal processing and controlling module, an optical transmitter module, and an optical receiver module; wherein the signal processing and controlling module controls the optical transmitter module to transmit an optical signal having a certain wavelength; the optical signal is injected into a medium to be measured; the optical signal is transmitted in the medium to be measured and delayed by the medium to be measured; after the optical signal delayed arrives at the optical receiver module, the optical receiver module transforms the optical signal delayed into an electrical signal, and the electrical signal is amplified and transmitted to the signal processing and controlling module by the optical receiver module; the signal processing and controlling module measures a delay time between transmitting the optical signal and receiving the optical signal; and a refractive index of the medium to be measured at the certain wavelength is calculated according to the delay time and a known length of the medium to be measured, comprising steps of:

(1) measuring a first delay time of an etalon, i.e., $t_1$, with the device for measuring refractive index of medium based on optical delay technology, wherein a refractive index and a length of the etalon are respectively known as $n_1$ and $L_1$;

(2) replacing the etalon with a medium to be measured, and measuring a second delay time $t_2$ with other factors unchanged, wherein a refractive index and a length of the medium to be measured are respectively denoted as $n_2$ and $L_2$;

(3) calculating an additional delay time of an optical signal with $\Delta t = t_1 - t_2$, wherein the additional delay time is caused by the medium to be measured; and (4) calculating the refractive index $n_2$ of the medium to be measured with a formula, i.e., $\Delta t = (n_1 \cdot L_1 - n_2 \cdot L_2)/c$, wherein $n_2 = (n_1 \cdot L_1 - c \cdot \Delta t)/L_2$, where $c = 3 \times 10^8$ m/s, i.e. the speed of light in vacuum.

2. The device for measuring refractive index of medium based on optical delay technology, as recited in claim 1, wherein the etalon is a medium having the known refractive index and the length, air or vacuum.

* * * * *